(12) United States Patent
Bibian et al.

(10) Patent No.: US 8,515,522 B2
(45) Date of Patent: Aug. 20, 2013

(54) ELECTRODE KIT FOR EASY AND FAST DEPLOYMENT IN ELECTROENCEPHALOGRAM ACQUISITION AND MONITORING APPLICATIONS

(75) Inventors: Stéphane Bibian, Cleveland Heights, OH (US); Tatjana Zikov, Cleveland Heights, OH (US)

(73) Assignee: NeuroWave Systems Inc., Cleveland Heights, OH (US)

( * ) Notice: Subject to any disclaimer, the term of this patent is extended or adjusted under 35 U.S.C. 154(b) by 260 days.

(21) Appl. No.: 13/110,533

(22) Filed: May 18, 2011

(65) Prior Publication Data

US 2011/0295099 A1 Dec. 1, 2011

Related U.S. Application Data

(60) Provisional application No. 61/348,154, filed on May 25, 2010.

(51) Int. Cl.
*A61B 5/0478* (2006.01)
(52) U.S. Cl.
USPC .......................... 600/383; 600/391; 600/392
(58) Field of Classification Search
USPC ......................................... 600/391, 392, 383
See application file for complete search history.

(56) References Cited

U.S. PATENT DOCUMENTS

| | | | |
|---|---|---|---|
| 4,090,752 A | 5/1978 | Long | |
| 4,595,013 A * | 6/1986 | Jones et al. | 600/383 |
| 5,352,315 A * | 10/1994 | Carrier et al. | 600/396 |
| 5,479,934 A | 1/1996 | Imran | |
| 6,115,638 A | 9/2000 | Groenke | |
| 6,394,953 B1 | 5/2002 | Devlin et al. | |
| 6,415,170 B1 | 7/2002 | Loutis et al. | |
| 7,689,278 B2 | 3/2010 | Jonsen | |
| 2002/0019588 A1 | 2/2002 | Marro et al. | |
| 2002/0183605 A1 | 12/2002 | Devlin et al. | |
| 2004/0162586 A1 | 8/2004 | Covey et al. | |

* cited by examiner

*Primary Examiner* — Lee S Cohen
(74) *Attorney, Agent, or Firm* — Brian M. Kolkowski; Robert Knecht Schmidt

(57) ABSTRACT

Electrodes for use in electroencephalographic recording, including consciousness and seizure monitoring applications, have novel features that speed, facilitate or enforce proper placement of the electrodes, including aligning tabs and arrowed aligning juts, color coding, and an insulating bridge between reference and ground electrodes which ensures a safe application distance between the conductive regions of the two electrodes in the event of cardiac defibrillation. A method of using a set of four such electrodes is also disclosed.

20 Claims, 7 Drawing Sheets

Stratum corneum
Stratum granulosum
Stratum spinosum
Stratum basale
Stratum lucidum

16

ELECTRODE KIT FOR EASY AND FAST DEPLOYMENT IN ELECTROENCEPHALOGRAM ACQUISITION AND MONITORING APPLICATIONS

CROSS-REFERENCE TO RELATED APPLICATIONS

This application claims priority to U.S. Provisional Patent application Ser. No. 61/348,154, which was filed on May 25, 2010.

BACKGROUND OF THE INVENTION (1) Field of the Invention

The present invention relates to sensors for fast and easy deployment in electroencephalogram acquisition and monitoring applications, including consciousness and seizure monitoring. The present invention further relates to electrodes for measuring biopotentials. The present invention further relates to groups or sets of sensors having individual features which facilitate their fast and correct placement and use and/or hinder or preclude their incorrect placement and use, without requiring extensive preparation of a patient's skin.

(2) Description of Related Art

Consciousness monitoring encompasses the field that uses measurements of biopotentials or other biological signals to gauge the level of consciousness or alertness of a subject or patient, especially in applications such as anesthesia monitoring or testing for seizure or other brain dysfunction or injury. Consciousness monitoring is frequently based on electroencephalographic (EEG) measurements.

In a typical diagnostic or monitoring study, a set of electrodes will be applied to the subject or patient. Proper design of electrodes and their placement is often critical to the reliability, accuracy, and/or repeatability of biopotential measurements and their analysis by the sophisticated monitoring equipment into which their signals are fed; variations in electrode placement or improper electrode placement or improper electrode spacing may mar the study if the analysis equipment is dependent upon proper placement, and may even unnecessarily endanger the patient in the event that a cardiac defibrillation shock is applied to the patient during consciousness monitoring. Traditionally, sets of electrodes are used in which all of the electrodes are essentially identical to each other in appearance. The similarity in some cases can result in electrode confusion on the part of the physician or technician applying the electrodes. Common mistakes in electrode placement include a mix-up between left-side and right-side electrode placement on the patient, a mix-up between signal and ground electrodes on the patient, incorrect placement of the electrodes on the patient in relation to the optimal or desired placement sites, placement of electrodes too near to each other or too far from each other, or placement of the electrodes in wrong or sub-optimal orientations with respect to each other. Extreme cases of misplacement result in entirely different electrode placement montages being used, but even minor misplacement can have a significant impact on the study or test results since the artifact processing, feature estimation, and suppression detection methods of test equipment or study methods can be sensitive to electrode placement. For example, too-short interelectrode distance can result in very small amplitude signals resembling suppression observed in some patients. Manufacturers of consciousness monitoring equipment have introduced specific sensors to address the problem of improper electrode placement and facilitate proper signal acquisition. Previous disclosures in this field of art include U.S. Pat. Nos. 6,032,064 to Devlin et. al., 6,301,493 B1 to Marro et al., 6,950,698 B2 to Sarkela et al., and U.S. Patent Application Publication No. 2004/0193068 A1 to Burton et al., all of which are herein incorporated by reference.

However, the need still exists for novel systems and methods which better facilitate fast and accurate electrode placement and use and/or hinder or preclude their incorrect placement and use. It is envisioned that once seizure detectors are as common appliances in workplaces and schools as are emergency cardiac defibrillators today, it will be critical for persons of no special training to perform fast and accurate electrode placement. It is therefore an object of the present invention to provide a novel electrode kit for easy and fast deployment in electroencephalogram acquisition and monitoring applications.

BRIEF SUMMARY OF THE INVENTION

In some embodiments, the present invention is an electrode for consciousness monitoring. Preferably, the electrode has a front, a back, and bottom, top, left, and right sides.

Preferably, each electrode is constructed of at least two separate structures: a physiological recording electrode and insulating region or adhesive collar. The electrode preferably comprises these two structures, but is constructed in a single unit which is able to be removed from the packaging and deployed onto a subject's skin. The physiological recording electrode can be of any type currently known in the art or later developed which is capable of conducting and recording physiological signals from a subject. The physiological recording electrode preferably comprises an upper surface and a lower surface. The upper surface is preferably that which is intended to face away from the subject when applied to said subject, and preferably will comprise an electrode connector (described herein). The lower surface is preferably that face of the physiological electrode which, when applied to a subject or patient, comes in contact with the subject's skin and receives and conducts the physiological signal from the subject to the monitoring equipment. The lower surface may optionally further comprise at least one surface feature which serves to either penetrate the subject's stratum corneum or to otherwise reduce electrode impedance and increase the quality of the physiological signal by bypassing factors that inhibit signal recording, such as the stratum corneum and the subject's hair. The physiological recording electrode is described in greater detail below.

The insulating region or adhesive collar may be of any insulating material known in the art, but preferably is a material that is pliant and comfortable to wear, such as polyester foam. This insulating region or adhesive collar preferably comprises two surfaces: an outer surface and an adhesive surface. The outer surface is that face of the insulating region or adhesive collar which, when placed on a subject's skin, faces outward and is capable of being viewed by the wearer, a user, or some other clinician. The adhesive surface is the face of the insulating region or adhesive collar which, when place on a subject's skin, comes in contact with the skin and cannot be seen. Preferably, at least part of the adhesive surface of the electrode is adhesive or sticky for application to skin. Again, the adhesive or method of sticking the electrode can be of any type known in the art such as acrylic adhesive. Preferably, the adhesive is capable of sticking to the skin for long periods of time (on the order of 1-24 hours) without losing adhesion and can be removed without undue pain to the wearer.

Preferably, the electrode has a colored label on the electrode front or on the outer surface of the insulating region or adhesive collar, allowing easy identification to prevent misplacement. The label may be printed directly onto the outer surface of the insulating region or adhesive collar material or may be printed onto a separate thin sheet and applied to the outer surface of the insulating region or adhesive material with an adhesive by any means known in the art. The label may also be stamped, etched, marked, engraved, burned, or affixed to the outer surface of the insulating region or adhesive collar material by any other means known in the art. The insulating region or adhesive collar material may also be manufactured in such a way as to have the label embossed in the surface of the outer surface of the insulating region or adhesive collar material.

Preferably, the electrode has a tab. Preferably the tab is upward-pointing in relation to the electrode's intended placement orientation. Preferably, the back of the tab is not adhesive or sticky, allowing the tab to be used as a handle in the application and removal of the electrode. The tab must be of sufficient size to be easily grasped between a typical human forefinger and thumb, i.e., no less than 0.2 inches in either its width or height dimensions. Preferably the tab is roughly triangular in shape, optionally with a rounded top, and measures 0.510 inches wide at its base and 0.218 inches tall. Preferably the tab is made out of the same material as, and is one with, the insulating region or adhesive collar material of the electrode (e.g., foam).

Preferably, the electrode label has one or more alignment indicators. The alignment indicators preferably correspond to a direction or an alignment in which the electrode is preferred to be oriented when applied to the subject or patient. The alignment indicators may be dots, lines, arrows, crosses, daggers, or any other symbols or configuration of markings, etchings, or stampings which can show both position and orientation. Preferably, the alignment indicator is an arrow. Preferably, it is of sufficiently bold and outstanding character as to be readily visible. The alignment indicator must not be just a negligibly thin hatch mark or seam. Preferably, the stalk of the arrow is more than one millimeter in width and more than 5 millimeters in length, the head of the arrow is more than five millimeters wide at its base, and the arrow is of a solid color that contrasts with the rest of the label color. Also, preferably, the electrode has on one or more of its sides a jut, and the electrode label has at the position of the jut and pointing in the direction of the jut a corresponding alignment indicator (e.g., arrow). In some embodiments, preferably, the electrode and its label have only one such jut and corresponding alignment indicator. Also preferably, the electrode has both a handling tab (as described above) and exactly one jut and corresponding alignment indicator such that the angle between the tab and the jut distinguish the electrode as unique among several such electrodes in a set, each having a different angle between tab and jut. For example, one electrode may have a 90° (clockwise) angle between tab and jut, whereas another has a 180° (clockwise) angle between tab and jut, whereas a third might have a 270° (clockwise) angle between tab and jut, helping to distinguish the three electrodes and diminish the chance of confusion between electrodes with regards to their placement on a patient in an electrode montage. Preferably, the arrow or other alignment indicator is applied to a patient such that it points at some distinctive feature, such as down at the bridge of the nose from the middle of the forehead, or to the corner of the eye from the temple.

The electrode may be a physiological electrode of any type known in the art. In some embodiments, the electrode is preferably a pre-gelled electrode having a spongy well of electrically conductive gel. In other embodiments, the electrode is preferably a dry electrode having surface features capable of penetrating the stratum corneum of the skin, for example of the type described in U.S. Pat. No. 7,286,864 B1 to Schmidt et al. or any of its related applications, all of which are herein incorporated by reference. In other embodiments the electrode may be a combined gel/penetrator electrode.

The electrode should have a connector for connecting to an electrode lead. In some embodiments the connector is preferably a standard electrode snap connector. The standard electrode snap connector consists of a single round conductive button, usually metal, with a diameter of approximately 3.9 millimeters at its widest point and approximately 3.73 millimeters at its thinned midsection, which comes approximately 2.7 millimeters down from the button top. Having a standard snap connector permits the use of standard leads at low cost. In other embodiments the connector is a snap connector that is larger or smaller or different in shape than a standard electrode snap connector. Having a snap connector that varies in size or shape from a standard connector enforces the use of a non-standard lead known to have superior performance characteristics such as better shielding for lower noise, or various other proprietary improvements. Furthermore, having a snap connector that varies in size or shape from a standard connector enforces the use of the electrode as electrodes with a standard connector will not mate with the non-standard electrode lead, which precludes the use of other electrodes that may yield suboptimal signal quality. Also, using snap connectors of different sizes and/or shapes for each electrode in the electrode kit helps further uniquely differentiate among the electrodes and prevent wrong connections. Standard connectors are round in shape, but if a different-shaped connector would be desired, it could be triangular, square, rectangular, pentagonal, hexagonal, octagonal, or shaped like stars of 3, 4, 5, 6, 7, or 8 points.

In some embodiments, two of the above-described electrodes are conjoined by their mutual foam insulating region or adhesive collar. In such an embodiment, the planar distance between the conductive regions of the two electrodes is enforced by the continuous insulating region or adhesive collar between the two conductive regions. This continuous insulating region or adhesive collar forms a kind of insulating bridge between the two electrodes. Preferably, this distance is at least the minimum effective distance for preventing electrical conduction between the two electrodes during cardiac defibrillation. The known and preferred minimum effective distance is 17 millimeters. "Planar distance" as referred to in this specification means the linear distance as measured when the electrodes lie flat in a plane, and not, for example, when they are folded up upon each other.

In some embodiments, the present invention comprises a set of electrodes for biosignals measurement for consciousness monitoring. Each electrode in the set may have any or all of the features described above. Preferably, the set comprises at least four electrodes, including a first electrode for the patient's right temple, a second electrode for the patient's left temple, a reference electrode, and a ground electrode. Each electrode has a front, a back, and bottom, top, left, and right sides. Each electrode back has a conductive region surrounded by an insulating region or adhesive collar.

As described previously, preferably, at least part of the back of each electrode is adhesive or sticky for application to skin.

Preferably, each electrode has a label on the electrode front, each label being visually distinct from the labels of the other electrodes, and the labels having the characteristics previously described in this disclosure. The feature providing the visual distinction may be color, pattern, reflectivity, or any other visually distinguishable feature or combination of features, but preferably it is color, and so preferably each electrode label has a unique color. The unique color label on each electrode helps the user to identify the desired location and position for each given electrode. Any set of colors may be selected for the electrode, but for example, preferably, the right temple electrode label is orange in color, the reference electrode label is beige in color, the ground electrode label is gray in color, and the left temple electrode label is yellow in color. The difference in colors helps prevent confusion of the electrodes during placement, and further assists in proper and faster electrode placement with the use of an easy-to-use electrode placement map having a color legend. The electrode placement map and legend is preferably provided with the packaging of the electrodes. Furthermore, each electrode lead should preferably echo the color of the corresponding electrode it mates with in order to facilitate easy and correct connection.

Preferably, all of the electrodes in the set are provided on a single sheet of thin plastic, styrene, or similar material, and each electrode easily peels off. Further preferably, the electrodes are positioned or ordered on the plastic or styrene sheet in roughly the same arrangement they are intended to be applied to the patient, for example, with the right temple electrode on the left of the sheet, and the bridged reference and ground electrodes in the middle of the sheet, and the left temple electrode on the right of the sheet, providing for a helpful spatial correspondence between original packaging placement and eventual placement of the electrodes on the patient.

Preferably at least three of the at least four electrodes each have an upward-pointing pointed tab at the electrode top of the type described previously, the back of the tab not being adhesive or sticky, each tab having sufficient size to be grasped between a human forefinger and thumb. If two or more electrodes are joined by one or more insulating bridges, as with the reference and ground electrodes in some embodiments, the two or more electrodes may share only one handling tab.

One or more of the electrodes in the set also preferably have the orientation juts and alignment indicators as described previously. For example, preferably, in the set, the right temple electrode has on its right side a rightward-pointing jut, and the right temple electrode label has at the position of the rightward-pointing jut and pointing in the direction of the rightward-pointing jut a corresponding rightward-pointing alignment arrow. Also preferably, in the set, the left temple electrode has on its left side a leftward-pointing jut, and the left temple electrode label has at the position of the leftward-pointing jut and pointing in the direction of the leftward-pointing jut a corresponding leftward-pointing alignment arrow. Also preferably, in the set, the reference electrode has on its bottom side a downward-pointing jut, and the reference electrode label having at the position of the downward-pointing jut and pointing in the direction of the downward-pointing jut a corresponding downward-pointing alignment arrow. If two or more electrodes are joined by one or more insulating bridges, as with the reference and ground electrodes in some embodiments, the two or more electrodes may share only one orientation jut and/or alignment arrow.

Also preferably in the set of electrodes, the reference and ground electrodes are conjoined by the insulating bridge described above. In such a case, the planar distance between the conductive regions of the reference electrode and the ground electrode is enforced by a continuous insulating region or adhesive collar between the two conductive regions, and said distance is at least the minimum effective distance for preventing electrical conduction between the two electrodes during cardiac defibrillation.

In some embodiments, preferably, each electrode has an independent connector for connecting to an electrode lead, and further preferably, at least one connector is a standard electrode snap connector. Having independent connectors, and having all of the connectors be snap connectors, enforces or conduces the application of pressure to the electrode after its application to the patient during the attachment of snap electrode leads, sealing the electrode to the skin surface, applying the gel and/or pressuring in the electrode penetrators, if any, to provide for good signal conductance and improved signal quality, as well of good adhesion of the electrode to the skin for longer-term use. In some embodiments, one or more of the connectors is not a standard electrode snap connector. It may be a snap connector of slightly larger or small size or different shape than standard to provide for the advantages described above.

This application also discloses a method of using the electrode set described above comprising the steps of peeling the right temple electrode from a backing and applying the right temple electrode to the right temple of a patient such that the alignment arrow on the right temple electrode label aligns with the eye line of the patient and points to the right side of the patient's right eye; peeling the left temple electrode from a backing and applying the left temple electrode to the left temple of the patient such that the alignment arrow on the left temple electrode label aligns with the eye line of the patient and points to the left side of the patient's left eye; peeling the reference and ground electrodes from a backing and applying the reference electrode to the middle forehead of the patient approximately 1.5 inches above the patient's eye line such that the alignment arrow on the reference electrode label aligns with the midline of the patient and points downward toward the patient's nose, and applying the ground electrode tot he left forehead of the patient at the distance from the reference electrode enforced by continuous insulating region or adhesive collar between the two conductive regions of the reference electrode and ground electrode; applying electrode leads to the individual electrodes; and using biopotentials measured by the electrodes to monitor the consciousness of the patient. The distance of "approximately 1.5 inches" can be measured as the combined width of the index, middle and ring fingers as measured at the fingertips, as indicated in FIG. 6, though for those with wider fingers, two fingers may suffice. It will be appreciated that the first three steps of applying the electrodes may be performed in any order with respect to each other.

One embodiment of the present invention is set of electroencephalographic monitoring electrodes comprising at least four electrodes, including a first electrode for the patient's right temple, a second electrode for the patient's left temple, a reference electrode, and a ground electrode, each electrode having a front, a back, and bottom, top, left, and right sides, each electrode back having a conductive region surrounded by an insulating region, at least part of the back of each electrode being adhesive or sticky for application to skin, each electrode having a label on the electrode front, each label being visually distinct from the labels of the other electrodes, at least three of the at least four electrodes each having an upward-pointing pointed tab at the electrode top, the back of the tab not being adhesive or sticky, each tab having sufficient size to be grasped between a human forefinger and thumb, the right temple electrode having on its right side a rightward-pointing jut, and the right temple electrode label having at the position of the rightward-pointing jut and pointing in the direction of the rightward-pointing jut a corresponding rightward-pointing alignment arrow, the left temple electrode having on its left side a leftward-pointing jut, and the left temple electrode label having at the position of the leftward-pointing jut and pointing in the direction of the leftward-pointing jut a corresponding leftward-pointing alignment arrow, the reference electrode having on its bottom side a downward-pointing jut, and the reference electrode label having at the position of the downward-pointing jut and pointing in the direction of the downward-pointing jut a corresponding downward-pointing alignment arrow, wherein the planar distance between the conductive regions of the reference-electrode and the ground electrode is enforced by a continuous insulating region between the two conductive regions, and said distance is at least the minimum effective distance for preventing electrical conduction between the two electrodes during cardiac defibrillation.

Another embodiment of the present invention is a method of using a set of electroencephalographic monitoring electrodes comprising the steps of before or after either of the following two steps, peeling a right temple electrode from a backing and applying the right temple electrode to a patient having a forehead, a right temple, a left temple, an eyeline, and a right and left eye, such that an alignment arrow on a label on the right temple electrode aligns with the eye line of the patient and points to the right side of the patient's right eye, after or before the preceding step or the following step, peeling a left temple electrode from a backing and applying the left temple electrode to the left temple of the patient such than an alignment arrow on a label on the left temple electrode aligns with the eye line of the patient and points to the left side of the patient's left eye, after or before either of the preceding two steps, peeling a reference and a ground electrode from a backing and applying the reference electrode to the middle forehead of the patient approximately 1.5 inches above the patient's eye line such that an alignment arrow on a label on the reference electrode aligns with a midline of the patient and points downward toward the patient's nose, and applying the ground electrode to the left forehead of the patient at the distance from the reference electrode enforced by a continuous insulating region between two conductive regions of the reference electrode and ground electrode, applying electrode leads to the individual electrodes, and using biopotentials measured by the electrodes to monitor the electroencephalogram of the patient.

Another embodiment of the present invention is an electrode for electroencephalographic monitoring, the electrode having a front, a back, and bottom, top, left, and right sides, the electrode back having a conductive region surrounded by a foam insulating region, at least part of the back of the electrode being adhesive or sticky for application to skin, the electrode having a colored label on the electrode front, the electrode having an upward-pointing pointed tab at the electrode top, the back of the tab not being adhesive or sticky, the tab having sufficient size to be grasped between a human forefinger and thumb, the electrode having on one of the sides a jut, and the electrode label having at the position of the jut and pointing in the direction of the jut a corresponding alignment arrow.

Still another embodiment of the present invention is an electrode for monitoring physiological signals that can be deployed quickly and easily comprising a physiological recording electrode comprising an upper surface and a lower surface, an adhesive collar comprising an outer surface and an adhesive surface, and an electrode label, wherein the label comprises an alignment indicator corresponding to a direction in which the electrode is to be oriented when placed on a subject.

Yet another embodiment of the present invention is a set of electrodes for monitoring physiological signals that can be deployed quickly and easily comprising at least four electrodes, each comprising a physiological recording electrode and an adhesive collar comprising an outer surface and an adhesive surface, wherein each physiological recording electrode comprises an upper surface with a connector and a lower surface, wherein each electrode has a label on the outer surface of the adhesive collar, the labels containing an alignment indicator corresponding to a direction in which each electrode assembly is to be oriented on a subject.

Still another embodiment of the present invention is a set of electrodes for monitoring physiological signals that can be deployed quickly and easily comprising at least four electrodes, each comprising a physiological recording electrode and an adhesive collar comprising a outer surface and an adhesive surface, wherein each physiological recording electrode comprises an upper surface with an independent connector and a lower surface, wherein each electrode has a label on the outer surface of the adhesive collar, the labels containing an alignment indicator corresponding to a direction in which each electrode assembly is to be oriented on a subject, wherein the connector on the upper surface of each physiological recording electrode has a distinct and unique shape in relation to the other electrodes connectors contained in the set.

Additional features and advantages of the invention will be set forth in the detailed description which follows, and in part will be readily apparent to those skilled in the art from that description or recognized by practicing the invention as described herein, including the detailed description which follows, the claims, as well as the appended drawings.

It is to be understood that both the foregoing general description and the following detailed description are merely exemplary of the invention, and are intended to provide an overview or framework for understanding the nature and character of the invention as it is claimed. The accompanying drawings are included to provide a further understanding of the invention, and are incorporated in and constitute a part of this specification. The drawings illustrate various embodiments of the invention and together with the description serve to explain the principles and operation of the invention.

DETAILED DESCRIPTION OF THE INVENTION

Figure 1:
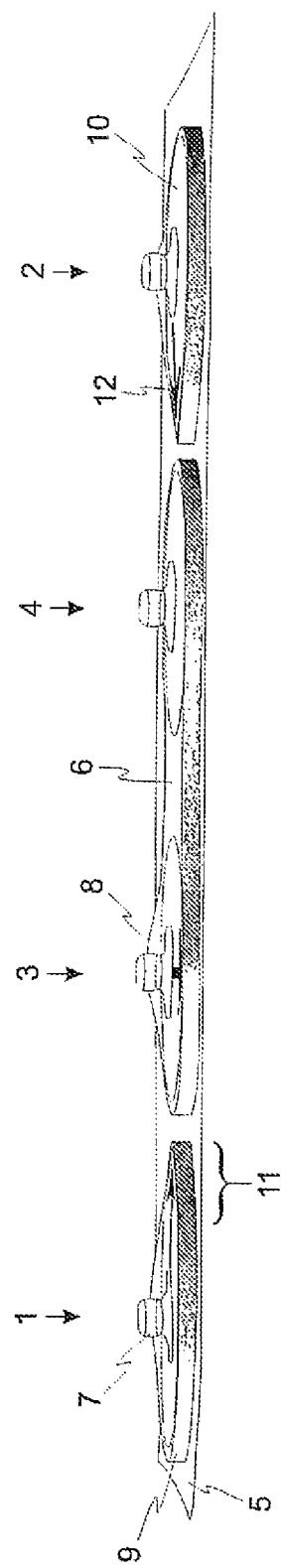
FIG. 1. Perspective view of an electrode set of the present invention from the bottom.

A preferred embodiment of the invention is illustrated and described. Four thin prepared electrodes come as a package as shown in FIG. 1. The right temple electrode 1 comes placed on the left side of a thin plastic, or similar material, backing sheet 5, and the left temple electrode 2 comes placed on the right side of the backing sheet. The reference electrode 3 and ground electrode 4 are conjoined by an insulating bridge 6. Each electrode has its own independent connector 7. As illustrated, the connectors are standard-size metal button or snap connectors, but as previously described, the connectors can be of any type or form factor known in the art. The right temple electrode, reference electrode and left temple electrode each have upward-pointing handling tabs 8 on their top sides. The handling tab is one and the same material as the foam insulating body structure 9 of the electrode with the exception that the handling tab is not backed with an adhesive like the rest of the electrode insulating body structure. This allows the tab to be bent frontward and grasped between the forefinger and thumb to more easily peel the electrode from the backing sheet 5 or to peel it off the subject when done. The insulating body structure is foam having a thickness of $1/16$ inch in the illustrated embodiment, but in variations can be made of other insulating, pliant material and can be any practicable thickness. Each electrode also has a printed label 10. In the illustrated embodiment, the labels are printed stickers that each have an adhesive backing and are applied to the foam insulating body structure, but as described previously, the labels can take a variety of other forms and be manufactured and/or applied in any other ways known in the art. The insulating body structure of the left temple, right temple, and reference electrodes also have orientation juts 11 which are simply protrusions out from the rounded bodies of the electrodes. As with the handling tabs, the orientation juts are one and the same material as the foam insulating body structure 9. On each label, at the location and in the orientation of the jut beneath it, a bold arrow 12 is printed as a readily visible guide for correct electrode placement. Preferably, the electrodes are also conveniently packaged with an electrode skin prep pad (not shown), e.g., a very mildly abrasive paper or thin cloth pad saturated with rubbing alcohol or similar, which can be used to clean and prepare the electrode sites on the surface of the skin prior to application of the electrodes.

Figure 2:
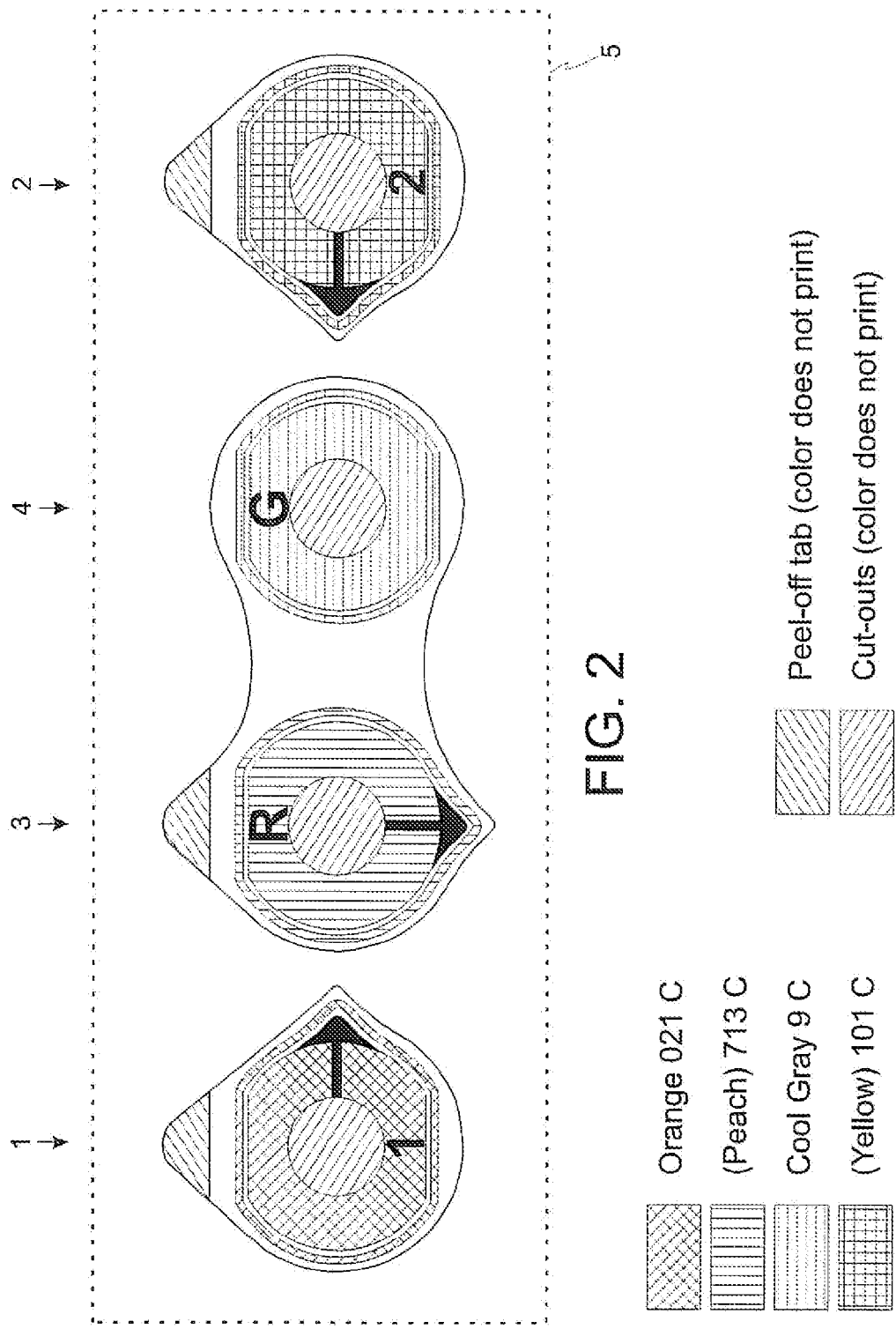
FIG. 2. Plan view of combined printing and cutting templates of the electrode set of the present invention from the front, with the backing sheet indicated by a dashed line.

The tabs and juts may be better seen in the plan view of FIG. 2, which combines the printing and cutting templates used in the manufacture of the electrode set of the present invention. The fronts of the electrodes are shown, and the backing sheet 5, which is not actually part of the printing or cutting templates, as indicated by a dashed line.

Figure 3:
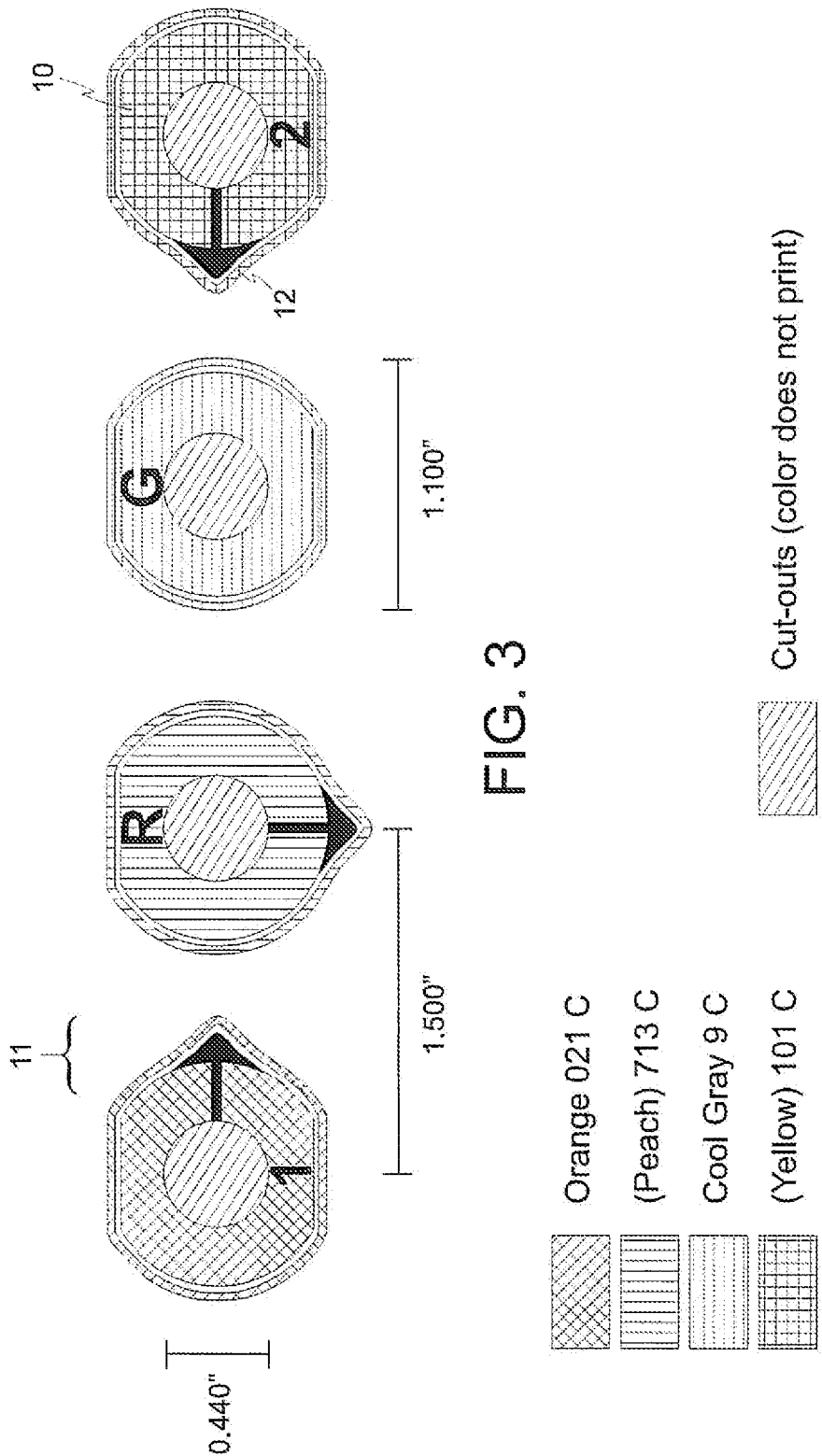
FIG. 3. Plan view of the label printing template of the electrode set of the present invention from the front.

FIG. 3 is a plan view of the label printing template used in the manufacture of the labels for the electrode set of the present invention. Different hatching patterns indicate the different colors used in the templates. The right temple electrode label is orange (preferably, Pantone color Orange 021 C), the left temple electrode label is yellow (preferably, Pantone 101 C), the reference electrode label is beige (preferably, Pantone 713 C) and the ground electrode is gray (preferably, Pantone Cool Gray 9 C). Cut-out holes are provided in the middle of each label for the electrode connectors. These holes are round and 0.440 inches in diameter. Excepting juts and flat tops and bottoms, the labels are round with widths of 1.100 inches. The labels are manufactured with center-to-center distances of 1.500 inches. The right temple electrode label is marked with a numeral 1, the left temple electrode label is marked with a numeral 2, the reference electrode label is marked with a letter R and the ground electrode label is marked with a letter G to assist in each recognition and proper designation and placement of electrodes. The labels may also have other markings indicating the manufacturer, brand or trade name, model number, serial number, expiration date, patient protection status, etc. The labels are backed with a permanent adhesive and are applied to the foam of the electrode body after printing.

Figure 4:
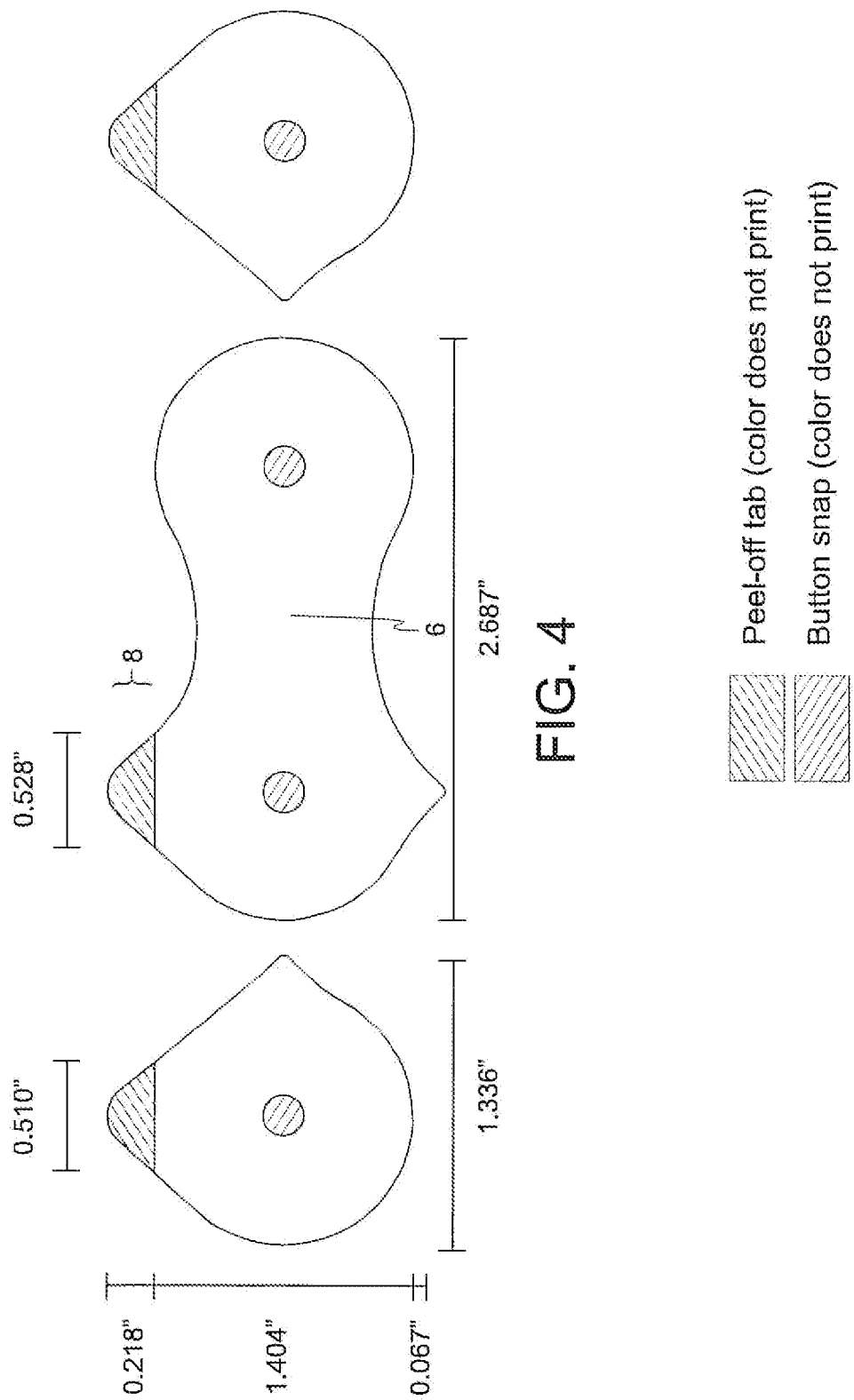
FIG. 4. Plan view of the foam cutting template of the electrode set of the present invention from the front.

FIG. 4 is a plan view of the foam cutting template used in the manufacture of the insulating body structures for the electrode set of the present invention. The handling tabs are 0.510 inches in width at the base, except for the handling tab of the reference electrode, which is 0.528 inches in width at the base, and are 0.218 inches in height. These dimensions are ample enough to allow the handling tabs to be easily grasped by the thumb and forefinger in order to peel the tabs off and manipulate the electrodes for placement. With the exception of the tabs and juts, the insulating body structures are 1.404 inches in height. The right and left temple electrodes are 1.336 inches wide and the conjoined reference and ground electrodes are 2.687 inches wide. Any electrically insulating, plaint material may be used for the insulating body structures, so long as it is biocompatible according to existing standards for surface electrodes in contact with the skin for 16 hours maximum application. The adhesive applied to the back of the foam is of an aggressive tackiness. The foam is $1/16$ inches in width. The foam is white in color. It will be appreciated that these details may vary and still be within the spirit of the present invention.

Figure 5:
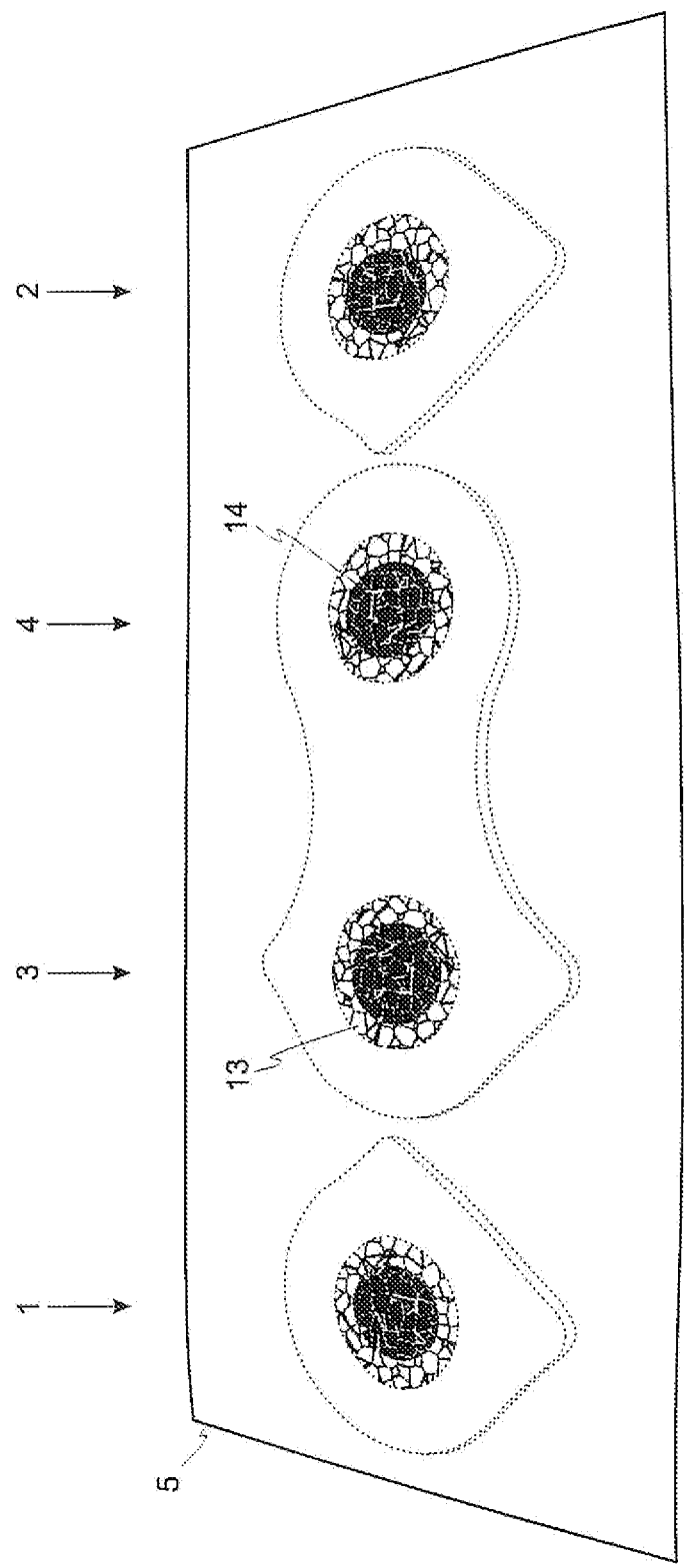
FIG. 5. Perspective view of an electrode set of the present invention from the back.

FIG. 5 illustrates a perspective view of an electrode set of the present invention from the back. The electrodes 1 2 3 4, rendered in dashed lines, are visible through the transparent or translucent backing sheet and the conductive regions of the electrodes comprising the gel-filled wells or reservoirs 13 surrounding the electrode proper 14 are visible. The round gel-filled wells 13, measuring about 0.64 inches in radius and having a depth nearly equal to the thickness of the insulating body structures, are filled with a light, thin sponge material saturated with a conductive gel. The electrode proper 14, visible in FIG. 5 as the black disc at the center of each well 13, is made of stainless steel or similar conductive metal or other conductive material. In the manufacture of the electrodes, the button connector 7 can be mated and crimped to the electrode proper 14 with the thinned top of the insulating body structures sandwiched in between, sealing the top of the well 13 and forming the electrode as unit having a gelled inside and a dry outside.

Once assembled and placed on the backing sheet, the electrodes can be packaged in a sealed paper pouch for distribution and can be stored on a shelf for some definite period of time if of the gelled type or an indefinite period of time if of the dry electrode type. Preferably, the gelled electrodes have a shelf life of at least a year without suffering a reduction in gel conductivity that would significantly impact sensor performance. More preferably, the shelf life is at least 2 years. Even more preferably, the shelf life is at least 5 years. An extended shelf life permits the electrode kit to be stored with a shelf-mounted emergency seizure detector for years and still work reliably when needed.

Figure 6:
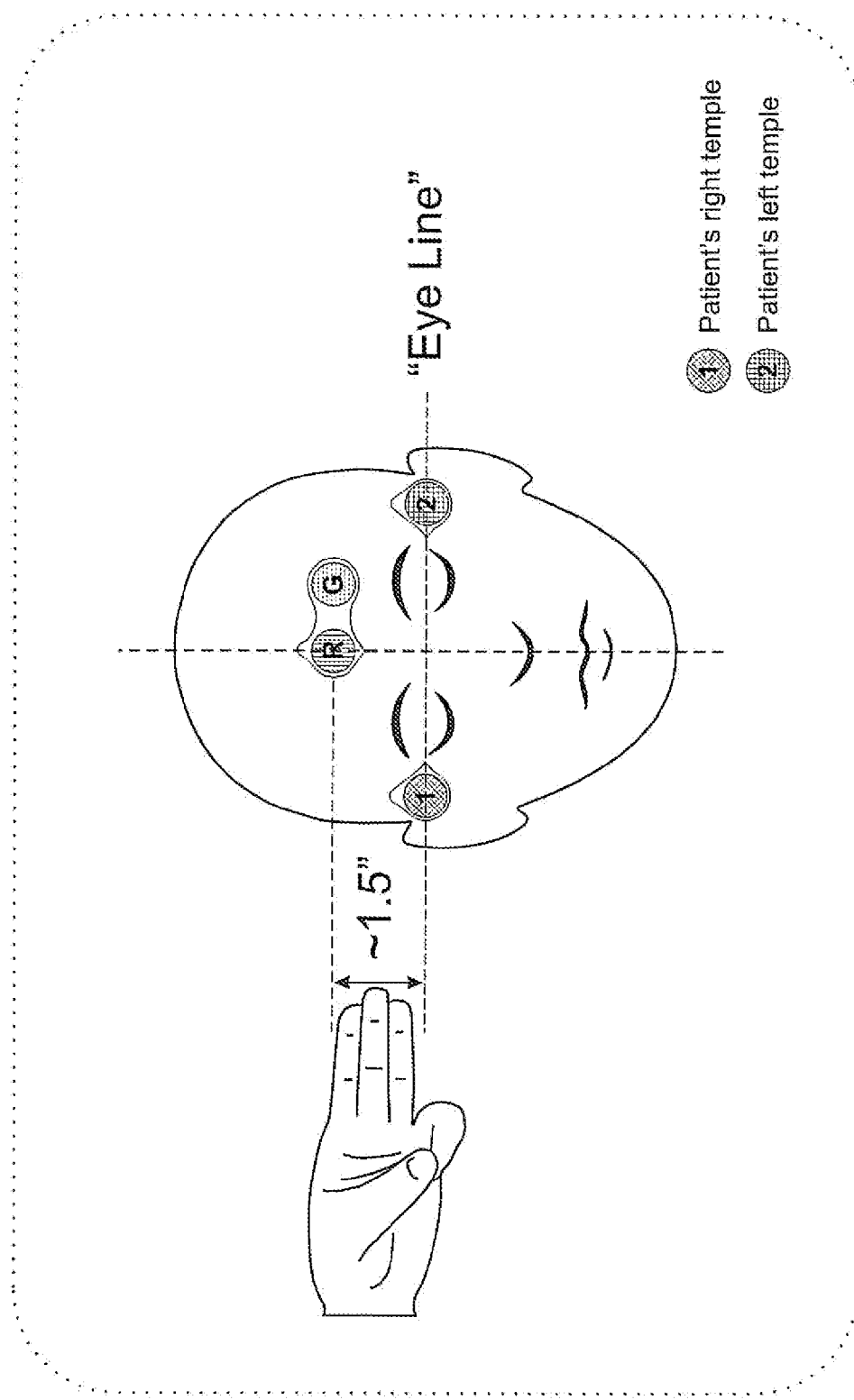
FIG. 6. Placement diagram for the electrode set of the present invention.

FIG. 6 shows the placement diagram for the electrode set of the present invention, intended to be shown on the packaging of the electrodes. Reference to the diagram facilitates fast and correct placement of the electrodes. As shown, the alignment arrows of the temple electrodes should align with the patient's eye line and the alignment arrow of the reference electrode should align with the patient's midline. The reference and ground electrodes should be placed on the forehead roughly 1.5 inches above the eye line. The placement diagram indicates a helpful guide for instantly and easily measuring the appropriate distance. The juts on the temple electrodes further help enforce appropriate distances in electrode placement. Because the reference and ground electrodes are conjoined by an insulation bridge, they help proof the setup against damage to the diagnostic equipment or patient injury from cardiac defibrillator impulses while also assuring accurate placement of the ground in relation to the reference. The color-coded electrodes reduce the chances that left and right electrodes are inadvertently mixed up by the physician or technician doing the electrode placement, or more importantly, the person of no special training in an emergency scenario and using a emergency seizure monitoring kit.

Figure 7:
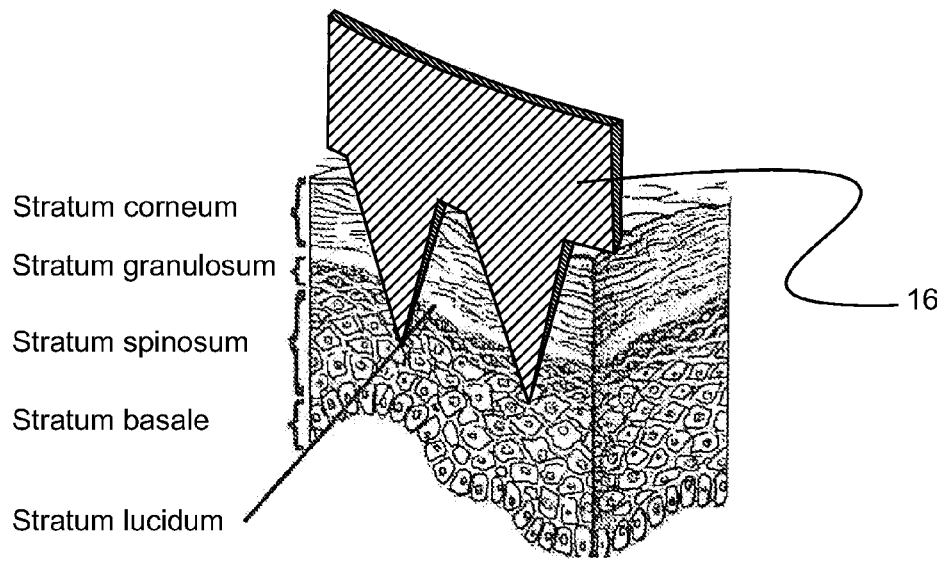
FIG. 7. Cross-sectional view of the epidermis layer and an illustration of the insertion of the penetrator(s) of the dry electrode used in some embodiments of the present invention.

FIG. 7 is a schematic illustrating the insertion of the penetrator(s) of the dry electrode used in some embodiments of the present invention into the epidermis. The penetrator(s) 16 are used to push through the high impedance upper layer or stratum corneum of the epidermis to reduce the contact impedance of the dry physiological electrode. Preferably, the penetrator(s) 16 also "lock" the electrode into the chosen skin region and thus reduce motion artifacts. The penetrator(s) 16 are further used for physiological sensing in the lower layers of the epidermis. The lower layers of the epidermis include the other layers below the stratum corneum of the epidermis. Physiological sensing generally is the sensing of electric potentials. The penetrator(s) 16 are used transmit the electric potential from the lower layers of the skin, particularly the epidermis and more particularly the stratum germinativum layer of the epidermis. The electric potential then can be measured by conventional measuring devices.

It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

What we claim is:

1. A set of electroencephalographic monitoring electrodes comprising:
   at least four electrodes, including a first electrode for the patient's right temple, a second electrode for the patient's left temple, a reference electrode, and a ground electrode, each electrode having a front, a back, and bottom, top, left, and right sides, each electrode back having a conductive region surrounded by an insulating region;
   at least part of the back of each electrode being adhesive or sticky for application to skin;
   each electrode having a label on the electrode front, each label being visually distinct from the labels of the other electrodes;
   at least three of the at least four electrodes each having an upward-pointing pointed tab that is an extension of the insulating region extended in the same plane as the insulating region, the back of the tab not being adhesive or sticky, each tab having sufficient size to be grasped between a human forefinger and thumb;
   the right temple electrode having on its right side a rightward-pointing jut, and the right temple electrode label having at the position of the rightward-pointing jut and pointing in the direction of the rightward-pointing jut a corresponding rightward-pointing alignment arrow;
   the left temple electrode having on its left side a leftward-pointing jut, and the left temple electrode label having at the position of the leftward-pointing jut and pointing in the direction of the leftward-pointing jut a corresponding leftward-pointing alignment arrow;
   the reference electrode having on its bottom side a downward-pointing jut, and the reference electrode label having at the position of the downward-pointing jut and pointing in the direction of the downward-pointing jut a corresponding downward-pointing alignment arrow;
   wherein the planar distance between the conductive regions of the reference electrode and the ground electrode is enforced by a continuous insulating region between the two conductive regions, and said distance is at least the minimum effective distance for preventing electrical conduction between the two electrodes during cardiac defibrillation.

2. The electrode set of claim 1, wherein each electrode label has a unique color.

3. The electrode set of claim 2, wherein the right temple electrode label is orange in color, the reference electrode label is beige in color, the ground electrode label is gray in color, and the left temple electrode label is yellow in color.

4. The electrode set of claim 1, wherein at least one electrode is a pre-gelled electrode having a spongy well of electrically conductive gel.

5. The electrode set of claim 1, wherein at least one electrode is a dry electrode having surface features capable of penetrating the stratum corneum of the skin.

6. The electrode set of claim 1, wherein each electrode has an independent connector for connecting to an electrode lead.

7. The electrode set of claim 6, wherein at least one connector is a standard electrode snap connector.

8. The electrode set of claim 7, wherein at least one connector is not a standard electrode snap connector.

9. A method of using a set of electroencephalographic monitoring electrodes comprising the steps of:
   before or after either of the following two steps, peeling a right temple electrode from a backing and applying the right temple electrode to a patient having a forehead, a right temple, a left temple, an eyeline, and a right and left eye, such that an alignment arrow on a label on the right temple electrode aligns with the eye line of the patient and points to the right side of the patient's right eye;
   after or before the preceding step or the following step, peeling a left temple electrode from a backing and applying the left temple electrode to the left temple of the patient such that an alignment arrow on a label on the left temple electrode aligns with the eye line of the patient and points to the left side of the patient's left eye;
   after or before either of the preceding two steps, peeling a reference and a ground electrode from a backing and applying the reference electrode to the middle forehead of the patient approximately 1.5 inches above the patient's eye line such that an alignment arrow on a label on the reference electrode aligns with a midline of the patient and points downward toward the patient's nose, and applying the ground electrode to the left forehead of the patient at the distance from the reference electrode enforced by a continuous insulating region between two conductive regions of the reference electrode and ground electrode;
   applying electrode leads to the individual electrodes; and using biopotentials measured by the electrodes to monitor the electroencephalogram of the patient.

10. The method of claim 9, wherein the electrode placement of each electrode having a label is determined by a unique color of the label on those electrodes.

11. The method of claim 9 wherein the reference and ground electrodes are joined by a mutual foam insulating region or adhesive collar and are peeled from the backing together as a single piece, and applied to the patient as a single piece.

12. The method of claim 9 wherein the electrodes are dry electrodes having surface features and are placed on the patient's skin allowing the surface features to pierce the stratum corneum of the patient's skin.

13. An electrode for electroencephalographic monitoring, the electrode having a front, a back, and bottom, top, left, and right sides, the electrode back having a conductive region surrounded by a foam insulating region, at least part of the back of the electrode being adhesive or sticky for application to skin, the electrode having a colored label on the electrode front;

the electrode having an upward-pointing pointed tab that is an extension of the insulating region extended in the same plane as the insulating region, the back of the tab not being adhesive or sticky, the tab having sufficient size to be grasped between a human forefinger and thumb;

the electrode having on one of the sides a jut, and the electrode label having at the position of the jut and pointing in the direction of the jut a corresponding alignment arrow.

14. An electrode of claim 13 conjoined to a second electrode for electroencephalographic monitoring having a conductive region surrounded by a foam insulating region, the two electrodes being conjoined by continuous mutual foam insulating regions, the first electrode being a reference electrode and the second electrode being a ground electrode, wherein the planar distance between the conductive regions of the two electrodes is enforced by the continuous insulating region between the two conductive regions, and said distance is at least the minimum effective distance for preventing electrical conduction between the two electrodes during cardiac defibrillation.

15. The electrode of claim 13, wherein the electrode label is orange, beige, or yellow in color.

16. The electrode of claim 13, wherein the electrode is a pre-gelled electrode having a spongy well of electrically conductive gel.

17. The electrode of claim 13, wherein at the electrode is a dry electrode having surface features capable of penetrating the stratum corneum of the skin.

18. The electrode of claim 13, wherein the electrode has a connector for connecting to an electrode lead.

19. The electrode of claim 18, wherein the connector is a standard electrode snap connector.

20. The electrode of claim 18, wherein the connector is a snap connector that is larger or smaller or different in shape than a standard electrode snap connector.

\* \* \* \* \*